United States Patent [19]

Rolfes

[11] Patent Number: 4,481,941

[45] Date of Patent: Nov. 13, 1984

[54] UNIVERSAL HIP STABILIZATION DEVICE

[76] Inventor: Thomas A. Rolfes, 1823 Enola Ct., St. Louis, Mo. 63122

[21] Appl. No.: 472,921

[22] Filed: Mar. 7, 1983

[51] Int. Cl.³ .............................................. A61F 3/00
[52] U.S. Cl. .................................... 128/87 R; 128/88
[58] Field of Search ...................... 128/87 R, 88, 89 R, 128/80 F, 80 G, 80 R

[56] References Cited

U.S. PATENT DOCUMENTS

| | | | |
|---|---|---|---|
| 2,753,864 | 7/1956 | Weidemann, Jr. | 128/87 R |
| 3,993,056 | 11/1976 | Rabischong et al. | 128/89 R |
| 4,088,130 | 5/1978 | Applegate | 128/80 F |
| 4,169,467 | 10/1979 | Rabischong et al. | 128/80 G |

FOREIGN PATENT DOCUMENTS 1324883  12/1963  France ............................. 128/80 F

*Primary Examiner*—John D. Yasko
*Attorney, Agent, or Firm*—Rogers, Eilers, Howell, Renner, Moore & Haferkamp

[57] ABSTRACT

A hip stabilization device is adaptable to all patients, and has a hinged brace held in alignment with the hip joint by a belt adjustably engaged about the patient's waist, with the belt engaging the top of the brace. A support is adjustably engaged about the patient's thigh, and is secured to the bottom of the brace. The mounting of the upper and lower parts of the brace to the belt and support respectively are adjustable to accommodate the height and proportions of the patient. The brace prevents rotation of the hip joint and lateral motion of the leg. The range of motion of the hinge is adjustable to permit the maximum flexion consistent with the patient's injury and proper stabilization of the joint. The attachment on the belt to mount the brace is such that when the belt is turned over, it can engage a brace on the other side of a patient. The support and brace are universal to fit the patient's other leg and hip, so that the same parts can be used to support either hip joint.

16 Claims, 12 Drawing Figures

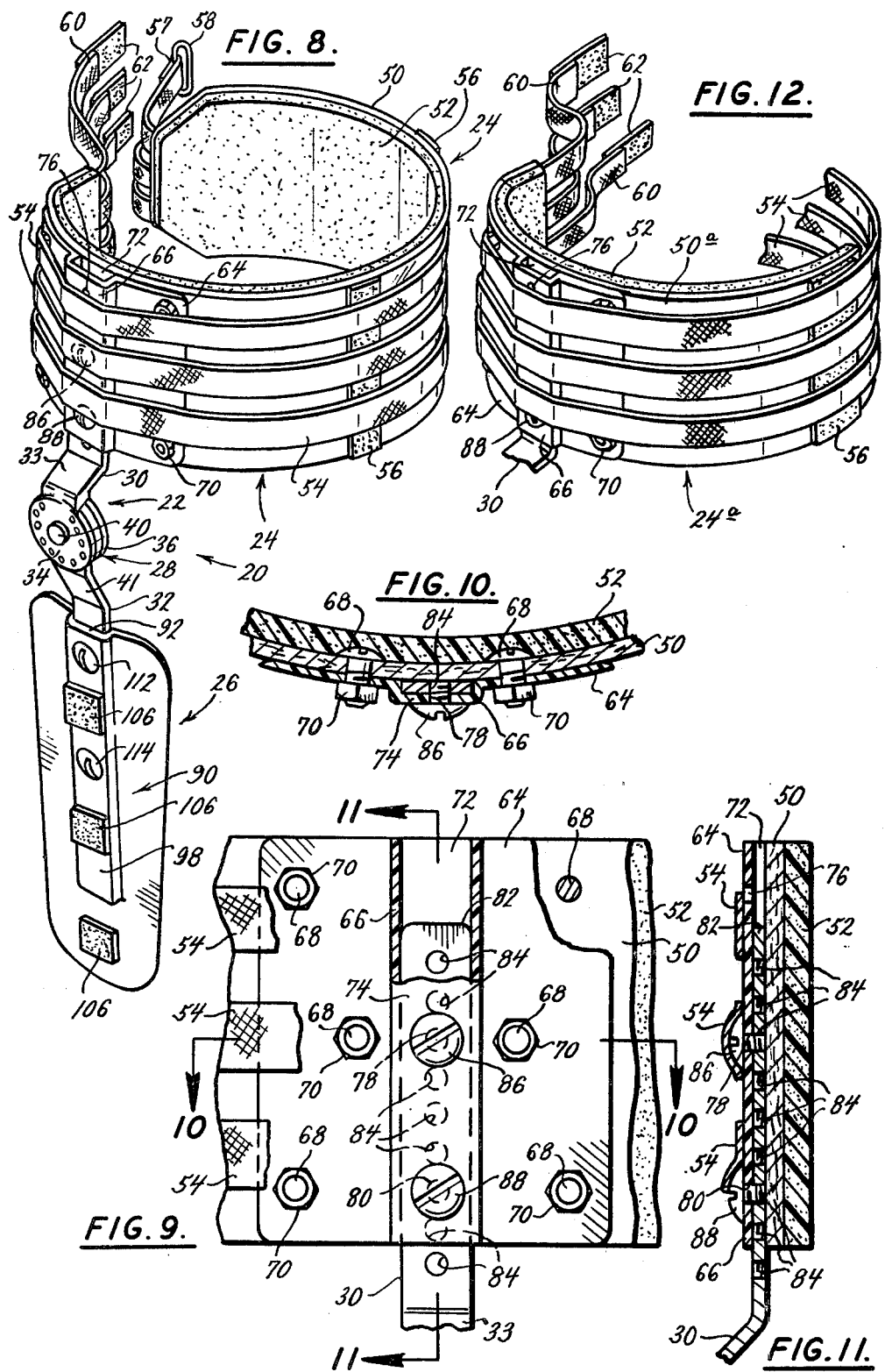

UNIVERSAL HIP STABILIZATION DEVICE

BACKGROUND OF THE INVENTION

This invention relates to orthopaedic hip braces and in particular to hinged braces to stabilize a hip joint during healing.

Before this invention, a patient suffering from a hip injury was typically put in a cast. While the cast served the purpose of stabilizing the hip joint, it presented many problems.

The casts were bulky, heavy, and cumbersome. The patient was fixed in a rigid position which made handling and transporting the patient difficult. Thus, while in the cast, the patient's life was severely restricted. Often the patient was completely bedridden. Even proper bathing was impossible, which presented hygiene problems. Furthermore, the casts were notoriously uncomfortable.

A serious problem with the casts was the atrophy of the muscles and deterioration of joints caused by the complete immobilization for long periods of time. This debilitation affected not only the muscle and joints in the cast, but the surrounding muscles and joints which were not used while the patient was immobile. It was not uncommon that upon removal of the cast the patient was so weakened that the patient could not walk for months afterward, and had great difficulty in bending over for a long time afterward.

SUMMARY OF THE INVENTION

The hip stabilization device of this invention comprises a hinged brace held in alignment with the injured hip joint. A belt adjustably secured about the patient's waist has a mounting means, such as a sheath, to engage the top of the brace. A support adjustably secured about the patient's thigh has a mounting means, such as a sheath, to engage the bottom of the brace. In addition to providing broad adjustability, the fasteners on the belt and support are such that the device can be simply and quickly applied and removed. The brace is adjustably engaged in the belt and support mounting means so that the device is adjustable to the height and proportions of the patient.

The belt mounting means is designed to allow use of the brace on either hip with the same belt, brace, and support components. By turning the belt over, the belt mounting means, such as the sheath, can engage the brace on the other side of the patient. Thus only a small inventory of parts is required as each device is completely adaptable to any size patient, to support either hip joint.

The device prevents rotation of the hip joint, i.e., the direction of movement such as when one knee is moved to cross over the other knee. The device also prevents abduction motion of the leg, i.e., the direction of motion when the leg is moved outwardly to the side away from the center of the body.

The range of motion of the hinge on the brace is adjustable so that at all times the maximum flexion, that is raising of the knee, and extension, that is lowering of the knee, consistent with the patient's injuries is permitted. In the preferred embodiment, this adjustment is provided by having upper and lower brace extensions with the lower portion of the upper extension having a plurality of circularly arranged holes about the hinge pin, and at least one limiting pin or screw extending through a pair of the circularly arranged holes to block and limit the pivoting motion of the lower brace extension. The limiting pin or screw can be selectively placed to prevent any flexion of the knee at all, such as is desired during the first three weeks or so after setting of the brace for a patient with a fracture of the proximal femur which is nondisplaced. After three weeks or so, the limiting pin or screw can be replaced to another pair of holes to allow flexion of the hip over a 15°–20° range. The amount of flexion motion can be adjusted with the progress of healing. The controlled motion that the hinge permits helps to prevent the muscles from atrophying and the joint from deteriorating.

The device is of elegant and inexpensive construction, and is light weight and compact. The detachability of the thigh support, the brace, the belt, and the straps used to secure the thigh support and belt, allow for the device to be stored in a small space. Because of the detachability of the components, if one component, such as the brace, is broken, another like brace can be interchanged therewith to work with the rest of the components of the device. Thus replacement costs are lessened, and ease of replacement is enhanced. The device is easily applied to the patient and can be concealed under loose clothing. The device is also easily removed to permit bathing or therapy.

BRIEF DESCRIPTION OF THE DRAWINGS

FIG. 8 is an orthogonal projection of the device;

FIG. 9 is a partial side view of the waist engaging means of the device showing the adjustable brace-engaging means, with some parts broken;

FIG. 10 is a cross sectional view, taken along line 10—10 in FIG. 9, showing the adjustable brace engaging means;

FIG. 11 is a cross sectional view, taken along line 11—11 in FIG. 9, showing the adjustable brace-engaging means;

FIG. 12 is an orthogonal projection of a modification of the waist engaging means.

DESCRIPTION OF THE PREFERRED EMBODIMENT

Figure 1:
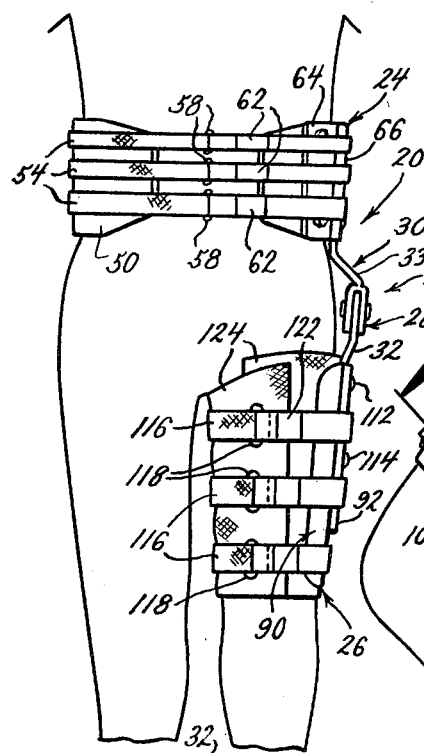
FIG. 1 is a front view of a hip stabilization device of this invention as it would be worn by a patient.
Figures 2, 6, 7:
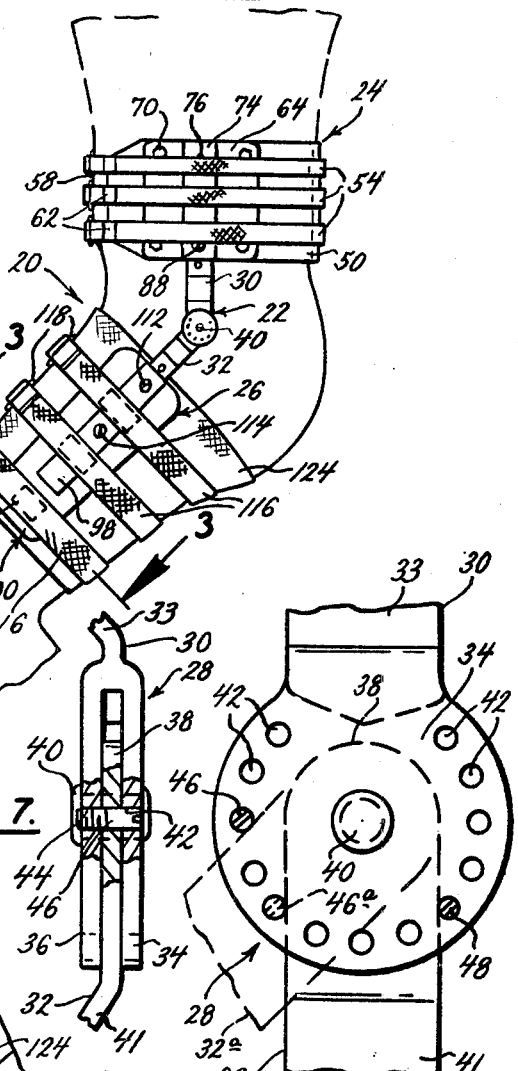
FIG. 2 is a side view of the device as it would be worn by a patient.
FIG. 6 is an exterior side view of the adjustable hinge on the brace.
FIG. 7 is a front view of the adjustable hinge on the brace taken from the left of FIG. 6.
Figure 4:
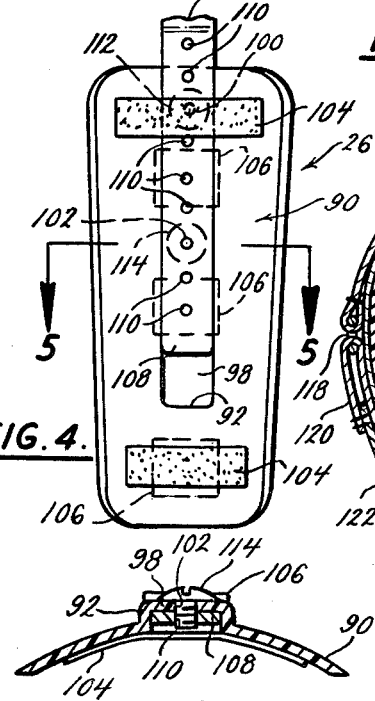
FIG. 4 is an inside side view of the thigh engaging means of the device showing the adjustable brace-engaging means.
Figures 3, 5:
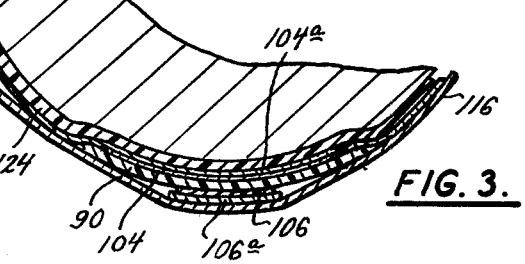
FIG. 3 is a partial cross sectional view, taken along line 3—3 in FIG. 2, showing the attachment of the device to the patient's thigh.
FIG. 5 is a cross sectional view, taken along line 5—5 of FIG. 4, of the thigh engaging means.

A universal hip stabilization device of this invention 20, is shown as it would be worn by a patient in FIGS. 1 and 2. The device comprises an adjustable hinged brace 22, a waist engaging means 24 and a thigh engaging means 26 adjustably engaging the top and the bottom of brace 22, respectively, thereby holding the brace in alignment with the hip joint.

Brace 22 has a hinge 28 and comprises an upper extension member 30 and a lower extension member 32.

The lower portion of upper extension 30 is offset at 33 and thence bends downwardly to terminate into a pair of parallel circular plates 34 and 36. Rounded top 38 of lower extension 32 is pivotally engaged between plates 34 and 36 as by a hinge pin 40. The top 38 is offset from the lower part of extension 32 by an angled section 41, so that with offset section 33 of the upper extension 30, the entire hinge 28 is positioned outwardly away from the hip so as to not rub thereagainst. Plates 34 and 36 have a plurality of aligned holes 42 and 44, respectively, about their circumferences. Holes 44 in plate 36 are threaded, with one such hole being shown in FIG. 7. The range of rotation of lower extension 32 with respect to upper extension 30 can be selectively controlled by the placement of screws 46 and 48 through selected holes 42 and threaded into the corresponding hole 44, as is shown for one pair of holes 42 and 44 in FIG. 7.

Waist engaging means 24 comprises a flexible belt 50, which can be of leather, having an interior side lined with foam padding 52, which can be of synthetic plastic. Belt 50 is fastened to the patient with three straps 54 which encircle belt 50. Velcro (TM) latching material sewn to the inside of each strap 54 engages receptive Velcro (TM) patches 56 affixed to the exterior of belt 50 as by adhesive, so that straps 54 are secured to belt 50 at the point of the Velcro (TM) patches 56. One end of each strap 54 is looped at 57 and is sewn to itself with a ring 58 extending through the loop 57. The other strap end 60 has a tab 62 of Velcro (TM) latching material sewn thereto with the latching material facing outwardly. To secure each strap 54, the end 60 is passed through ring 58, and folded back against strap 54 to be secured thereto by the Velcro (TM) tab 62 engaging receptive Velcro (TM) sewn to the outside of strap 54, with such receptive Velcro (TM) extending a sufficient distance inwardly from the end 60 to allow for sufficient range in tightening each strap.

A modification of waist engaging means 24 is shown in FIG. 12. There the belt 50a is shorter. In this form the belt is more adaptable to patients with smaller waists. The fastening of the belt 50a is the same as described for belt 50, with the other parts otherwise being the same.

The adjustable engagement between brace 22 and waist engaging means 24 is shown in enlarged detail views in FIGS. 9, 10 and 11. The waist engaging means 24 further comprises a plate 64, which can be of rigid plastic or of metal, having a unitary rectangular channel 66 formed approximately in its middle, is attached to the exterior of belt 50 by nuts 70 and bolts 68 extending through the belt 50 so that channel 66 and belt 50 define a vertical rectangular sheath 72. The outwardly facing wall 74 of channel 66 has three equally spaced threaded holes 76, 78 and 80 for receiving screws to be described. Upper brace extension 30 has in its top portion 82 a plurality of equally spaced threaded holes 84, which are spaced so that as the upper extension 30 is moved telescopically within sheath 72, the holes 84 can be positioned to be aligned with the lower two channel holes 78 and 80. Two screws 86 and 88 are threaded through holes 78 and 80 of channel 66 and threaded through the aligned holes 84 of upper extension 30 to firmly mount brace upper extension 30 within sheath 66 and thereby mount brace 22 to belt 50.

Belt 50 can be turned over so that sheath 72 is positioned on the other side of the patient, which allows the one belt to engage the brace to support either hip joint. Upper extension 30 is telescopically received in sheath 72 on the other side of the patient, and is positioned so that holes 84 are aligned with the lower two holes in channel 66, now 76 and 78 because of the turning of belt 50. The two screws 86 and 88 are threaded into holes 76 and 78 of channel 66 and through the selected aligned threaded holes 84 of upper extension 30 to securely mount upper extension 30 within sheath 66 and thereby firmly mount brace 22 to belt 50.

Referring now more to FIGS. 2-5, and 8, thigh engaging means 26 comprises an arcuate shaped plastic support 90 which is shaped to conform to the natural curvature of the thigh. Support 90 has a unitary rectangular channel 92 formed approximately in its middle. The outwardly facing wall 98 of channel 92 is provided with two threaded holes 100 and 102 for receiving screws to be described. The inside of support 90 is provided with two patches 104 of Velcro (TM) latching material, secured thereto as by adhesive. The outside of support 90 is provided with three equally spaced patches 106 of Velcro (TM) latching material, secured thereto as by adhesive.

Lower brace extension 32 has in its bottom portion 108 a plurality of equally spaced threaded holes 110, which are spaced so that as the lower extension 32 is moved telescopically within channel 92, the holes 110 can be positioned to be aligned with holes 100 and 102 in channel 92. Two screws 112 and 114 are threaded into holes 100 and 102 of channel 92 and through the selected aligned threaded holes 110 of lower extension 32 to securely mount the lower extension 32 within channel 92 and thereby firmly mount the brace 22 to support 90. A backing plate (not shown) can be mounted on the inside of support 90, and secured thereto as by adhesive. The backing plate would thus define a vertical, rectangular sheath between the backing plate and support 90, to achieve a secure engagement between brace 22 and support 90.

Support 90 is fastened to the patient's thigh with three straps 116 which encircle support 90. The inside of each strap 116 is provided with a path of Velcro (TM) latching material 106a (FIG. 3) sewn to the inside of each strap 116 to engage the receptive Velcro (TM) patches 106 on the outside of support 90 to detachably secure the straps to support 90. One end of each strap 116 is looped as described for straps 54 to secure a ring 118. The other strap 116 end 120 has a tab 122 of Velcro (TM) latching material sewn thereto facing outwardly. To secure each strap 116, the end 120 passes through the ring 118, and is folded back against strap 116 to be secured thereto by the Velcro (TM) tab 122 which engages receptive Velcro (TM) (not shown) latching material sewn to the exterior of strap 116.

A separate protective synthetic plastic foam pad 124 can be interposed between the patient's thigh, and the support 90 and straps 116, by wrapping pad 124 around the patient's thigh. The exterior of pad 124 is lined with a layer 104a of Velcro (TM) latching material, with lining 104a engaging the receptive Velcro (TM) patches 104 to detachably secure pad 124 to support 90. Alternatively, permanent foam padding can be provided on the inside side of support 90.

Operation

In operation, the device can be applied to either side of the hip. For purposes of illustration, we assume that the left side of the hip area is injured, so that the device is applied by the operator to the left hip such as shown in FIGS. 1 and 2. For initial application, the belt 50, the brace 22, and the support 90 can all be detached from each other. Upon selection of the left side of the hip, the belt 50 is extended about the patient's waist so that the sheath 72 is aligned to extend downwardly towards the left hip joint. The belt 50 is then secured in place by the three straps 54 with each of the strap ends 60 extending through their corresponding rings 58 and folded back so that the Velcro (TM) tabs 62 latch with their corresponding Velcro (TM) latching material to give the straps 54 and the belt 50 a snug but comfortable fit.

The brace 22 can then be mounted to the sheath 72 and belt 50. When first applied, the limit screw 48 can be installed while the limit screw 46 can be removed so that the hinge 28 can pivot towards flexing the knee for ease of application. The operator takes the brace 22 and slides the upper brace extension 82 into the sheath 72 until two of the holes 84 in the upper brace portion 82 are aligned with holes 78 and 80 in channel side 74 at a point where the hinge 22 is aligned with the hip joint. The screws 78 and 80 can then be passed through the said holes as previously described to secure the upper brace extension 30 to the sheath 72 and belt 50.

Next, the thigh engaging means 26 can be secured about the thigh and to the brace 22. If it is desired to have the pad 124 applied to the patient's thigh, it is first wrapped around the thigh such as shown in FIG. 1.

The support 90 is then grasped by the operator's hand and moved upwardly from the knee towards the hip so that the lower brace extension 32 is slid into the channel 92 until holes 110 in lower brace extension 32, are in alignment with the holes 100 and 102 in the channel wall for the proper positioning of the support 90 against the thigh. Once the position for the support 90 is selected, screws 112 and 114 are inserted through the holes 100 and 102 and screwed therein as well as into the corresponding holes 110 in the brace extension 32 to secure extension 32 to the support as described previously.

The straps 116 are then passed around the support 90 so that the Velcro (TM) on the inside of each of the straps 116 is aligned with each of the Velcro (TM) patches 106 on the exterior of the support 90, and the ends of the straps 116 are secured by passing the strap ends 120 through the corresponding rings 118 and looping the ends 120 back to latch against the straps 116 as described previously.

Initially, during the time period immediately following the injury, it may be desired to limit hip movement. The device 20 can be thus fitted so that the brace extensions 30 and 32 extend in alignment with one another such as shown in FIG. 8, and as shown in solid lines in FIG. 6. To lock the brace extensions 30 and 32 in this position screw 48 is positioned as shown in FIG. 6 while screw 46 would be moved downward two of the holes 42 to be placed as shown as 46a. As the patient heals and flexion movement is allowed, the screw can be moved clockwise from position 46a to the next hole and eventually clockwise again to be positioned as shown in FIG. 6. Such positioning allows the lower brace extension 32 to move from the position shown in solid lines in FIG. 6 to the position shown in dashed lines in FIG. 6 as 32a. More flexion can be allowed by moving screw 46 farther clockwise from its FIG. 6 position.

The device 20 thus mounted as shown in FIGS. 1 and 2 prevents rotation of the hip joint, as in the crossing of the leg. Abduction, the sideways movement of the leg, is also prevented. Only flexion, the raising of the leg, and extension, the lowering of the leg, is permitted. The range of flexion and extension is completely adjustable to permit the maximum flexion and extension consistent with the patient's injuries. As the healing progresses, the range of flexion motion can be increased by more clockwise (FIG. 6) movement of the screw 46 in the holes such as previously described so that the muscles, tendons and joints do not atrophy during the healing process.

The device can be quickly detached by removing the straps 54 from engagement with the rings 58 about the belt 50, and removal of the straps 116 from the locking rings 118. The screws 112 and 114 can be removed from engagement with lower extension 32 and support 90 can then be slid downwardly away from lower brace extension 32 to remove extension 32 from channel 92 and disengage support 90 from the brace 22. Likewise the screws 86 and 88 can be removed from sheath 72 and the upper brace extension 30 slid downwardly out of sheath 72 to disengage the brace 22 therefrom.

The use of the smaller waist engaging means shown as 24a in FIG. 12 with the shorter belt 50a is the same as described heretofore for belt 50.

The components thus can be separately stored or can be stored together in disassembled form to take up much less space than in the connected form. The device can be reused on a patient with an injury associated with the right hip by simply flipping the belt over so that the sheath 72 is positioned on the right side of the patient and so that the hole 76 is now the lower of the three holes 76, 78 and 80 in the channel wall 74. The sheath 72 is then aligned with the right hip in the same fashion as described for the left hip, and the hinge 28, and the support 90 and pad 124 are also aligned and attached as described previously.

However although the hinge limit screws 46 and 48 likewise are positioned on the right hip to first resist flexion, the movement of the screws 46 and 48 are the reverse of that described for the left side, with the screw 46 remaining in position 46a as shown looking at the exterior of the hinge in FIG. 6, and with the screw 48 being moved counterclockwise about the hinge 28 in the holes 42 and 44 to permit a greater range of flexion.

The belt straps 54, are detachable from the belt 50, its padding 54 and mounting plate 64, and the belt 50 is likewise detachable from the brace 32. The brace 32 is in turn detachable from the thigh support 90, and the straps 118 and pad 124 are detachable from one another and from support 90. This interchangability of the various components in advantageous in that should one of them become damaged and need replacement, it is necessary to replace only that component rather than to bring the entire unit in for repair. This facilitates maintenance and enhances the ease of operability. Thus only the single component need be shipped to the manufacturer for repair. The detachability of the components also brings about the universal applicability of the device to the right or left hip.

The detachability of the various components further enhances storage in that, if desired, the entire unit can be disassembled and all the components stored in one compartmentalized area. On the other hand, detachability of components allows multiple units of the devices to be stored with the braces stored in one compartment, the thigh supports stored in another compartment, and so on. Thus, greater stock can be maintained of components which show a tendency to wear out sooner than the other components.

I claim:

1. A device for stabilizing the hip of a patient who has a broken bone in the leg or hip or has a dislocated hip, but who retains control of the muscles in the leg and hip, the device interacting with the muscles of the leg and hip to permit the patient to voluntarily move his leg to various positions, comprising:

(a) a brace for mounting in alignment with the patient's hip; said brace having an upper extension and a lower extension, and means for pivotally connecting the lower extension to the upper extension;

(b) noninflatable waist engaging means for adjustably engaging the patient's waist, and noninflatable means for adjustably engaging the upper extension to the waist engaging means so that the device can be adjusted to patients of varying heights and proportions;

(c) noninflatable thigh engagement means for adjustably engaging the patient's thigh comprising a rigid support, and noninflatable means for adjustably engaging the bottom of the lower extension to the thigh engagement means so that the device can be adjusted to patients of varying heights and proportions, so that the brace is held generally in alignment with the hip joint to allow the patient to use the muscles in his leg and hips to pivot the lower extension with respect to the upper extension in the same direction as the flexion of the hip; and (d) further comprising means for adjustably selectively limiting the pivoting of the lower extension with respect to the upper extension so that different degrees of pivoting of the two extensions to each other are provided.

2. The device of claim 1 wherein the means for limiting the pivoting comprises a limiting member mounted to one of said extensions so that the other extension contacts said limiting member to be restricted in pivoting farther when said extensions are pivoted a predetermined distance one to the other.

3. The device of claim 1 wherein the bottom of the upper extension has a plurality of aligned holes about its periphery, and the lower extension of the brace is pivotally mounted to the upper extension bottom, and wherein the means for selectively limiting the pivoting of the lower extension with respect to the upper extension comprises at least one limiting member for placement in the holes to block movement of the lower extension so that the pivoting of the lower extension with respect to the upper extension can be selectively limited by placement of the limiting member through the holes in the bottom of the upper extension.

4. A universal device for stabilizing a patient's hip, to be mounted in alignment with the hip comprising:

(a) an upper extension;
(b) a lower extension;
(c) means for pivotally mounting the top portion of the lower extension to the bottom portion of the upper extension;
(d) means for selectively limiting the range of pivoting of the lower extension with respect to the upper extension;
(e) waist engagement means for adjustably engaging the patient's waist comprising a belt at least partially encircling the patient's waist, and means for adjustably securing the belt about the patient's waist;
(f) thigh engagement means for adjustably engaging the patient's thigh;
(g) means for adjustably engaging the top portion of the upper extension to the waist engagement means comprising a vertical sheath associated with the belt for receiving the upper extension and means for adjustably engaging the upper extension in the sheath, and means for adjustably engaging the bottom portion of the lower extension to the thigh engagement means so that the upper extension and lower extension are held generally in alignment with the hip joint, with the pivoting of the lower extension with respect to the upper extension in the same direction as flexion of the hip; and the vertical belt sheath having first and second ends, and being open at its first and second ends so that the belt sheath can receive the top of the upper extension through the first belt sheath end when the belt sheath is on one side of the patient's hip and wherein the belt can be turned over and the belt sheath located on the opposite side of the patient's hip so that the belt sheath can receive the top of the upper extension through the second belt sheath end so that the same belt and belt sheath can be used on either side of the patient.

5. The device of claim 4 wherein the means for adjustably engaging the patient's thigh comprises a support, and means for adjustably securing the support to the patient's thigh.

6. The device of claim 4 wherein the means for adjustably engaging the bottom of the lower extension to the thigh engaging means comprises a sheath associated with the support for receiving the lower extension, and means for adjustably engaging the lower extension in the support sheath.

7. The device of claim 4 wherein the means for limiting the pivoting comprises a limiting member mounted to one of said extensions so that the other extension contacts said limiting member to be restricted in pivoting farther when said extensions are pivoted a predetermined distance one to the other.

8. The device of claim 6 wherein the means securing the belt is at least one strap engaging the belt and adjustably fastened about the patient's waist with Velcro (TM) fastening material.

9. The device of claim 6 wherein the means securing the support is at least one strap engaging the support and adjustably fastened about the patient's thigh with Velcro (TM) fastening material.

10. The device of claim 6 wherein the top of the upper extension has a plurality of holes, and wherein the means adjustably engaging the upper extension in the belt sheath is at least one fastening member passing into the belt sheath and into a hole in the upper extension.

11. The device of claim 6 wherein the bottom of the lower extension is provided with a plurality of holes, and wherein the means adjustably engaging the lower extension in the support sheath is at least one fastening member passing through the support sheath and into a hole in the lower extension.

12. A universal device for stabilizing a patient's hip, to be mounted in alignment with the hip comprising:

(a) an upper extension having a bottom section having a plurality of aligned holes;
(b) a lower extension;
(c) a pin pivotally mounting the top of the lower extension to the bottom of the upper extension;
(d) at least one limiting member for placement in a selected hole in the bottom of the upper extension to block movement of the lower extension, so that the pivoting of the lower extension with respect to the upper extension can be selectively limited by placement of the limiting member through a selected hole in the bottom of the upper extension;

(e) a belt at least partially encircling the patient's waist;

(f) means for securing the belt about the patient's waist;

(g) means for adjustably engaging the upper extension in the sheath;

(h) a support for the thigh;

(i) means for securing the support against the patient's thigh;

(j) a vertical sheath associated with the support to receive the bottom of the lower extension;

(k) means adjustably engaging the lower extension in the support sheath so that the upper extension and lower extension are held generally in alignment with the hip joint to allow the pivoting of the lower extension with respect to the upper extension in the same direction as flexion of the hip; and (l) a vertical sheath mounted on the belt to receive the top of the upper extension, the belt sheath having first and second ends and being open at its first and second ends, so that the belt sheath can receive the top of the upper extension through the first belt sheath end when the belt sheath is on one side of the patient's hip and wherein the belt can be turned over and the belt sheath located on the opposite side of the patient's hip so that the belt sheath can receive the top of the upper extension through the second belt sheath end to allow the same belt and belt sheath to be used on either side of the patient.

13. A device for stabilizing the hip of a patient who has a broken bone in the leg or hip or has a dislocated hip, but who retains control of the muscles in the leg and hip, the device interacting with the muscles of the leg and hip to permit the patient to voluntarily move his leg to various positions, comprising:

(a) a brace for mounting in alignment with the patient's hip, said brace having an upper extension and a lower extension, and means for pivotally connecting the lower extension to the upper extension;

(b) noninflatable waist engaging means for adjustably engaging the patient's waist, and noninflatable means for adjustably engaging the upper extension to the waist engaging means so that the device can be adjusted to patients of varying heights and proportions, comprising a belt at least partially extending about the patient's waist, and means to mount the upper brace extension to the belt;

(c) noninflatable thigh engagement means for adjustably engaging the patient's thigh, and noninflatable means for adjustably engaging a bottom portion of the lower extension to the thigh engagement means so that the device can be adjusted to patients of varying heights and proportions, so that the brace is held generally in alignment with the hip joint to allow the patient to use the muscles in his leg and hips to pivot the lower extension with respect to the upper extension in the same direction as the flexion of the hip;

(d) the upper extension having an upper portion for attachment to the belt, the upper extension portion extending downwardly into an outwardly extending portion and thence extending downwardly into a lower portion, with the pivotal connection to the lower extension being with the said lower portion of the upper extension; and (e) means for selectively limiting the pivoting of the lower extension with respect to the upper extension so that different degrees of pivoting of the two extensions to one another are provided.

14. A device for stabilizing the hip of a patient who has a broken bone in the leg or hip or has a dislocated hip, but who retains control of the muscles in the leg and hip, the device interacting with the muscles of the leg and hip to permit the patient to voluntarily move his leg to various positions, comprising:

(a) a brace for mounting in alignment with the patient's hip, said brace having an upper extension and a lower extension, and a means for pivotally connecting the lower extension to the upper extension;

(b) noninflatable waist engaging means for adjustably engaging the patient's waist, and noninflatable means for adjustably engaging the upper extension to the waist engaging means so that the device can be adjusted to patients of varying heights and proportions, comprising a belt at least partially encircling the patient's waist and a vertical sheath associated with a belt for receiving the upper portion of the upper extension, and means for adjustably engaging the upper extension in the sheath;

(c) noninflatable thigh engagement means for adjustably engaging the patient's thigh, and noninflatable means for adjustably engaging the bottom of the lower extension to the thigh engagement means so that the device can be adjusted to patients of varying heights and proportions, so that the brace is held generally in alignment with the hip joint to allow the patient to use the muscles in his leg and hips to pivot the lower extension with respect to the upper extension in the same direction as that of flexion of the hip;

(d) means for selectively limiting the range of pivoting of the lower extension with respect to the upper extension so that different degrees of pivoting of the two extensions to each other are provided;

(e) the vertical belt sheath having first and second ends, and being open at its first and second ends so that the belt sheath can receive the top of the upper extension through the first belt sheath end when the belt sheath is on one side of the patient's hip and wherein the belt can be turned over and the belt sheath located on the opposite side of the patient's hip so that the belt sheath can receive the top of the upper extension through the second belt sheath end so that the same belt and belt sheath, the same brace, and the same thigh engagement means and means for engaging the lower extension to the thigh engagement means can be used on either side of the patient.

15. A device for stabilizing the hip of a patient who has a broken bone in the leg or hip or has a dislocated hip, but who retains control of the muscles in the leg and hip, the device interacting with the muscles of the leg and hip to permit the patient to voluntarily move his leg to various positions, comprising:

(a) a brace for mounting in alignment with the patient's hip, said brace having an upper extension and a lower extension, and means for pivotally connecting the lower extension to the upper extension;

(b) noninflatable waist engaging means for adjustably engaging the patient's waist, and noninflatable means for adjustably engaging the upper extension to the waist engaging means so that the device can be adjusted to patients of varying heights and proportions, comprising a belt at least partially extending about the patient's waist, and a sheath mounted to the belt for receiving an upper portion of the upper extension with means to attach the upper portion of the extension within the sheath;

(c) noninflatable thigh engagement means for adjustably engaging the patient's thigh comprising a rigid support, and noninflatable means for adjustably engaging a bottom portion of the lower extension to the rigid support so that the device can be adjusted to patients of varying heights and proportions, so that the brace is held generally in alignment with the hip joint to allow the patient to use the muscles in his leg and hips to pivot the lower extension with respect to the upper extension in the same direction as the flexion of the hip;

(d) the upper extension having an upper portion for insertion within the sheath, the upper extension portion extending downwardly into an outwardly extending portion and thence extending downwardly into a lower portion, with the pivotal connection to the lower extension being with the said lower portion of the upper extension;

(e) means for selectively limiting the pivoting of the lower extension with respect to the upper extension so that different degrees of pivoting of the two extensions to one another are provided; and (f) the belt sheath having first and second ends and being opened at its first and second ends, so that the belt sheath can receive the top of the upper extension through the first belt sheath end when the belt sheath is on one side of the patient's hip and wherein the belt can be turned over and the belt sheath located on the opposite side of the patient's hip so that the belt sheath can receive the top of the upper extension through the second belt sheath end to allow the same belt and belt sheath, the same brace and the same thigh engagement means, and means for engaging the lower extension to the thigh engagement means to be used on either side of the patient.

16. The structure of claim 12 wherein the bottom of the upper extension is generally circular and the plurality of aligned holes are spaced about the said bottom in a generally circular arrangement.

* * * * *

UNITED STATES PATENT OFFICE
CERTIFICATE OF CORRECTION

Patent No. 4,481,941      Dated November 13, 1984

Inventor(s) Thomas A. Rolfes

It is certified that error appears in the above-identified patent and that said Letters Patent are hereby corrected as shown below:

In column 6, line 49, the first occurrence of "in" should be -- is --.

Signed and Sealed this

Twenty-first Day of May 1985

[SEAL]

Attest:

DONALD J. QUIGG

Attesting Officer      Acting Commissioner of Patents and Trademarks